(12) United States Patent
Garovic

(10) Patent No.: US 9,213,038 B2
(45) Date of Patent: Dec. 15, 2015

(54) EARLY MARKER OF PROTEINURIA IN PATIENTS TREATED WITH AN ANTI-VEGF TREATMENT

(71) Applicant: Mayo Foundation for Medical Education and Research, Rochester, MN (US)

(72) Inventor: Vesna D. Garovic, Rochester, MN (US)

(73) Assignee: Mayo Foundation for Medical Education and Research, Rochester, MN (US)

( * ) Notice: Subject to any disclaimer, the term of this patent is extended or adjusted under 35 U.S.C. 154(b) by 0 days.

(21) Appl. No.: 13/898,124

(22) Filed: May 20, 2013

(65) Prior Publication Data
US 2013/0296397 A1 Nov. 7, 2013

Related U.S. Application Data

(63) Continuation of application No. 13/518,358, filed as application No. PCT/US2010/061543 on Dec. 21, 2010, now abandoned.

(60) Provisional application No. 61/288,514, filed on Dec. 21, 2009.

(51) Int. Cl.
*A61K 39/395* (2006.01)
*G01N 33/53* (2006.01)
*G01N 33/94* (2006.01)
*G01N 33/50* (2006.01)

(52) U.S. Cl.
CPC ............ *G01N 33/94* (2013.01); *G01N 33/5091* (2013.01); *G01N 2800/347* (2013.01); *G01N 2800/50* (2013.01); *G01N 2800/52* (2013.01)

(58) Field of Classification Search
None
See application file for complete search history.

(56) References Cited

U.S. PATENT DOCUMENTS

| | | | |
|---|---|---|---|
| 5,811,250 | A | 9/1998 | Solum et al. |
| 6,969,591 | B2 | 11/2005 | Hara |
| 7,435,419 | B2 | 10/2008 | Karumanchi et al. |
| 7,455,985 | B2 | 11/2008 | Stuart et al. |
| 7,713,705 | B2 | 5/2010 | Buechler et al. |
| 2003/0198959 | A1 | 10/2003 | Kurnit |
| 2006/0008804 | A1 | 1/2006 | Chibout et al. |
| 2006/0104902 | A1 | 5/2006 | Powis et al. |
| 2007/0178605 | A1 | 8/2007 | Mor et al. |
| 2008/0112960 | A1 | 5/2008 | Dorai |
| 2008/0255181 | A1 | 10/2008 | Oh et al. |
| 2009/0068683 | A1 | 3/2009 | Garovic |
| 2009/0104649 | A1 | 4/2009 | Garovic |
| 2013/0034861 | A1 | 2/2013 | Garovic |
| 2014/0030743 | A1 | 1/2014 | Garovic |
| 2014/0051185 | A1 | 2/2014 | Garovic |
| 2014/0302538 | A1 | 10/2014 | Garovic |
| 2014/0322721 | A1 | 10/2014 | Garovic |

FOREIGN PATENT DOCUMENTS

WO   WO 2013/181612   12/2013

OTHER PUBLICATIONS

Habara et al. 2008. Folia Biologica (Praha) 54:162-167.*
GenBank GI No. 11321634; Accession No. NP 036252.1, dated Nov. 27, 2005, 3 pages.
GenBank GI No. 116875767; Accession No. NP 003248.3, dated Oct. 31, 2006, 7 pages.
GenBank GI No. 2281027; Accession No. BAA21569.1, dated Jul. 24, 1997, 1 page.
GenBank GI No. 33598950; Accession No. NP 005388.2, dated May 7, 2006, 3 pages.
GenBank GI No. 4503131; Accession No. NP 001895.1, dated Jun. 4, 2006, 30 pages.
GenBank GI No. 47078292; Accession No. NP 000203.2, dated Jun. 4, 2006, 25 pages.
GenBank GI No. 66277202; Accession No. NP 001018121.1, dated May 7, 2006, 3 pages.
GenBank GI No. 7657465; Accession No. NP 056535.1, dated Mar. 2, 2006, 2 pages.
GenBank GI No. 7657615; Accession No. NP 055440.1, dated Dec. 18, 2005, 5 pages.
GenBank GI No. 4501881; Accession No. NP 001091.1, dated May 21, 2006, 5 pages.
European Search Report; Jun. 19, 2013; European Patent Office (EPO); 10842718.8; 2 pages.
Garovic et al; Urinary podocyte excretion as a marker for preeclampsia; Am J Obstet Gynecol; Apr. 2007; 196 (4):320.e1-7.
Izzedine et al; VEGF signalling inhibition-induced proteinuria: Mechanisms, significance and management; Dec. 2009/Jan. 2010; 46(2):439-448.
European Office Action in Application No. 10842718.8 mailed Jul. 12, 2013, 5 pages.
Authorized officer Je Hwan Chang, International Search Report/Written Opinion in PCT/US2009/64934 mailed Jul. 9, 2010, 5 pages.
International Preliminary Report on Patentability in International Application No. PCT/US2009/064934, mailed Jun. 3, 2011, 5 pages.
International Search Report and Written Opinion in International Application No. PCT/US2013/043727, mailed Oct. 18, 2013, 6 pages.
Office Action in U.S. Appl. No. 12/137,350, dated Mar. 11, 2013, 8 pages.
Office Action in U.S. Appl. No. 12/137,350, dated May 27, 2011, 8 pages.
Office Action in U.S. Appl. No. 12/137,350, dated Jun. 23, 2010, 8 pages.

(Continued)

*Primary Examiner* — Shulamith H Shafer
(74) *Attorney, Agent, or Firm* — Fish & Richardson P.C.

(57) ABSTRACT

This document provides methods and materials related to determining whether or not a human receiving a therapy (e.g., an anti-VEGF therapy such as a bevacizumab therapy) has developed or is at risk for developing proteinuria. For example, methods and materials for detecting urinary podocytes to determine whether or not a human receiving anti-VEGF therapy has or is at risk for developing proteinuria or kidney injury are provided.

7 Claims, 1 Drawing Sheet

(56) References Cited

OTHER PUBLICATIONS

Office Action in U.S. Appl. No. 12/137,350, dated Aug. 17, 2012, 7 pages.
Office Action in U.S. Appl. No. 12/137,350, dated Nov. 24, 2010, 9 pages.
Office Action in U.S. Appl. No. 12/137,350, dated Nov. 25, 2011, 8 pages.
Office Action in U.S. Appl. No. 12/274,117, dated Mar. 22, 2013, 11 pages.
Office Action in U.S. Appl. No. 12/274,117, dated Jun. 23, 2010, 11 pages.
Office Action in U.S. Appl. No. 12/274,117, dated Jun. 27, 2011, 13 pages.
Office Action in U.S. Appl. No. 12/274,117, dated Nov. 26, 2010, 11 pages.
Office Action in U.S. Appl. No. 12/274,117, dated Dec. 21, 2011, 8 pages.
Office Action in U.S. Appl. No. 14/019,895, dated Dec. 6, 2013, 13 pages.
Office Action in U.S. Appl. No. 14/032,361, dated Dec. 24, 2013, 23 pages.
Ahmed et al., Colocalisation of vascular endothelia growth factor and its Flt-1 receptor in human placenta, *Growth Factors*, 1995, 12:235-243.
Anonymous, "Report of the National High Blood Pressure Education Program Working Group on High Blood Pressure in Pregnancy," *Am. J. Obstet. Gynecol.*, 2000, 183(suppl):S1-S22.
Boseman, J. et al., "Microparticles Expressing Vascular Endothelial Growth Factor Receptor-1 (VEGR-1) Are Increased in Preeclampsia," *J. Am. Soc. Nephrol.*, 19, Abstract SA-PO2469 (2008).
Camici, "Urinary biomarkers of podocyte injury," *Biomarkers Med.*, 2008, 2(6):613-616.
Chaiworapongsa et al., "Evidence supporting a role for blockade of the vascular endothelial growth factor system in the pathophysiology of preeclampsia," *Am. J. Obstet. Gynecol.*, 2004, 190:1541-1550.
Charnock-Jones, Stephen D. et al., "Vascular Endothelial Growth Factor Receptor Localization and Activation in Human Trophoblast and Choriocarcinoma Cells," *Biology of Reproduction*, 1994, 51:524-530.
Collino et al. "Preeclamptic sera induce nephrin shedding from podocytes through endothelin-1 release by endothelial glomerular cells," *Am. J. Physiol Renal Physiol.*, 2008, 294(5):F1185-F1194.
DeLong et al., "Comparing the areas under two or more correlated receiver operating characteristic curves: a nonparametric approach," *Biometrics*, 1988, 44:837-845.
Garovic et al., "Glomerular expression of nephrin and synaptopodin, but not podocin, is decreased in kidney sections from women with preeclampsia," Nephrol. Dial. Transplant., 2007, 22(4):1136-1143.
Gonzalez-Quintero et al., "Elevated plasma endoethlial microparticles: Preeclampsia versus gestational hypertension," *Am. J. Obstet. Gynecol.*, 2004, 191:1418-1424.
Gonzalez-Quintero et al., "Elevated plasma endothelial microparticles in preeclampsia," *Am. J. Obstet. Gynecol.*, 2003, 189:589-593.
Goswami et al., "Excess syncytiotrophoblast microparticle shedding is a feature of early-onset pre-eclampsia, but not normotensive intrauterine growth restriction," *Placenta*, 2006, 27:56-61.
Hara, M. et al., "Podocyte Membrane Vesicles in Urine Originate from glomerular Podocyte Microvilli In Situ," *J. Am. Soc. Nephrol.*, 2008, 19, Abstract SA-PO2468.
Jones, "HELLP! A Cry for Laboratory Assistance: A Comprehensive Review of the HELLP Syndrome Highlighting the Role of the Laboratory," *Hematopathol. Mol. Hematol.*, 1998, 11:147-171.
Kanjanabuch, T. et al., "Urine Podocyte Predicts Steroid Responsiveness in Naïve Nephrotic Syndrome ," *J. Am. Soc. Nephrol.*, 2008, 19, Abstract SA-PO2467.
Karumanchi and Marshall, "Preeclampsia and the kidney: footprints in the urine," *Am. J. Obstet. Gynecol.*, 2007, pp. 287-288.

Kershaw et al., "Molecular Cloning and Characterization of Human Podocalyxin-like Protein: orthologous relationship to rabbit PCLP1 and rat podocalyxin," *J. Biol. Chem.*, 1997, 272(25):15708-15714.
Kihara et al., "Podocyte detachment and epithelial cell reaction in focal segmental glomerulosclerosis with cellular variants," *Kidney Int..*, 1997, 63(52):S171-S176.
Kikuno et al., "Prediction of the Coding Sequences of Unidentified Human Genes. XIV. The Complete Sequences of 100 New cDNA Clones from Brain Which Code for Large Proteins in vitro," *DNA Res.*, 1999, 6:197-205.
Knight et al., "Shedding of syncytiotrophoblast microvilli into the maternal circulation in pre-eclamptic pregnancies," *British J. Obstet. & Gynaecology*, 1998, 105:632-640.
Konijnenberg et al., "Extensive platelet activation in preeclampsia compared with normal pregnancy: Enhanced expression of cell adhesion molecules," Am. J. Obstetrics & Gynecology, 1997, 176:461-469.
Levine et al., "Circulating Angiogenic Factors and the Risk of Preeclampsia," *N. Engl. J. Med.*, 2004, 350:672-683.
Levine et al., "Soluble Endoglin and Other Circulating Antiangiogenic Factors in Preeclampsia," *N. Engl. J. Med.*, 2006, 355:992-1005.
Levine et al., "Urinary Placental Growth Factor and Risk of Preeclampsia," *JAMA*, 2005, 293:77-85.
Lok et al., "Microparticile-assocaiated P-selectin reflects platelet activation in preeclampsia," *Platelets*, Feb. 2007 18:68-72.
Lok, et al., "Circulating Platelet-derived and Placenta-derived Microparticles Expose Fit-1 in Preeclampsia," *Reproductive Sciences*, Oct. 20, 2008, 15:1002-1010.
Maynard et al., "Excess placental soluble fms-like tyrosine kinase 1 (sFlt1) may contribute to endothelial dysfunction, hypertension, and proteinuria in preeclampsia," *J. Clin. Invest.*, 2003, 111(5):649-658.
Mundel et al., "Rearrangements of the cytoskeleton and cell contacts induce process formation during differentiation of conditionally immortalized mouse podocyte cell lines," *Exp. Cell Res.*, 1997, 236:248-258.
Najafian, B. et al., "Podocyte Detachment (PCD) Does Not Precede Idiopathic Focal Segmental Glomerulosclerosis in Children," *J. Am. Soc. Nephrol.*, 2008, 19, Abstract SA-PO2466.
Nakamura et al., "Urinary excretion of podocytes in patients with diabetic nephropathy." *Nephrology Dialysis Transplantation*, 2000, 15:1739-1383.
Nakamura et al., "Urinary Podocytes for the Assessment of Disease Activity in Lupus Nephritis," *Am. J. Med. Sci.*, 2000, 320(2):112-116.
Neufeld et al., "Vascular endothelial growth factor (VEGF) and its receptors," *FASEB Journal*,1999, 13:9-22.
Nomura et al., "Platelet-derived microparticles may influence the development of atherosclerosis in diabetes mellitus," *Atherosclerosis*, 1995, 235-240.
Park et al., "An elevated maternal plasma, but not amniotic fluid, soluble fms-like tyrosine kinase-1 (sFlt-1) at the time of mid-trimester genetic amniocentesis is a risk factor for preeclampsia," *Am. J. Obstet. Gynecol.*, 2005, 193:984-989.
Petermann et al., "Podocytes that detach in experimental membranous nephropathy are viable," *Kidney Int.*, 2003, 64:1222-1231.
Rosenthal et al., "Podocyturia is a sensitive and specific marker for preeclampsia," *Am. J. Obstet. and Gyn.*, 2006, 195(6), Suppl 1:S36, Abstract 81.
Schiffer et al., "Apoptosis in podocytes induced by TGF-β and Smad7," *J. Clin. Invest.*, 2001, 108(6):807-816.
Selheim et al., "Identification of functional VEGF receptors on human platelets," *FEBS Lett.*, 2002 512:107-110.
Simon et al., "Receptors of vascular endothelial growth factor/vascular permeability factor (VEGF/VPF) in fetal and adult human kidney: Localization and [125I] VEGF binding sites," *J. Am. Soc. Nephrol.*, 1998, 9:1032-1044.
VanWijk et al., "Microparticle subpopulations are increased in preeclampsia: Possible involvement in vascular dysfunction?" *Am. J. Obsetet. Gynecol.*, 2002, 187: 450-456.
Villmow et al., "Markers of platelet activation and platelet-leukocyte interaction in patients with myeloproliferative syndromes," *Thrombosis Res.*, 2003, 108:139-145.

(56) References Cited

OTHER PUBLICATIONS

Vogelmann et al., "Urinary excretion of viable podocytes in health and renal disease," *Am. J. Physiol. Renal Physiol.*, 2003, 285:F40-F48.
Wang et al., "Increased urinary excretion of nephrin, podocalyxin, and βig-h3 in women with preeclampsia," *Am J Physiol Renal Physiol.*, 2012, 302(9):F1084-F1089.
Yu et al., "Urinary Podocyte Loss Is a More Specific Marker of Ongoing Glomerular Damage than Proteinuria," *J. Am. Soc. Nephrol.*, 2005, 16:1733-1741.
GenBank GI No. 7657615; Accession No. NP 055440.1, dated Jan. 6, 2013, 3 pages.
GenBank GI No. 66277202; Accession No. NP 001018121,1, dated Feb. 3, 2013, 3 pages.
GenBank GI No. 33598950:Accession No. NP 005388.2, dated Feb. 3, 2013, 3 pages.
GenBank GI No. 7271815; Accession No. AAF44629.1, dated Mar. 21, 2000, 1 page.
GenBank GI No. 7657465; Accession No. NP 056535.1, dated Feb. 2, 2013, 3 pages.
GenBank GI No. 10441644; Accession No. AAG17141.1, dated Oct. 1, 2000, 2 pages.
GenBank GI No. 33323347; Accession No. AA Q07403.1, dated Sep. 29, 2003, 1 page.
GenBank GI No. 14572521; Accession No. AAK00529.1, dated Jun. 27, 2001, 2 pages.
GenBank GI No. 885926; Accession No. AAA82892.1, dated Dec. 4, 1995, 2 pages.
GenBank GI No. 110611793; Accession No. AAH46461.2, dated Aug. 18, 2006, 2 pages.
GenBank GI No. 1321634; Accession No. NP 036252.1, dated Jan. 13, 2013, 4 pages.
GenBalik GI No. 4501881; Accession No. NP 001091.1, dated Feb. 9, 2013, 4 pages.
GenBank GI No. 3157976; Accession No. AAC17470.1, dated Nov. 22, 2000, 2 pages.
GenBank GI No. 2281027; Accession No. BAA21569.1, dated Dec. 14, 2007, 1 page.
GenBank GI No. 4503131; Accession No. NP 001895.1, dated Feb. 25, 2013, 8 pages.
GenBank GI No. 47078292; Accession No. NP 000203.2, dated Feb. 24, 2013, 4 pages.
GenBank GI No. 340237; Accession No. AAA61283.1, dated Jan. 14, 1995, 1 page.
GenBank GI No. 6682361; Accession No. AA.F23322.1, dated Jan. 8, 2000, 2 pages.
GenBank GI No. 704148; Accession No. AAC50104.1, dated Mar. 10, 1995, 2 pages.
GenBank GI No. 116875767; Accession No. NP 003248.3, dated Jan. 6, 2013, 7 pages.
Achenbach et al , "Parietal epithelia cells in the urine as a marker of disease activity in glomerular diseases," *Nephrol Dial Transplant*, 2008, 23:3138-3145.
Camici, "Urinary detection of podocyte injury," *Biomed and Parmacotherap.* 2007, 61:245-249.
George et al., "Nephrotic syndrome after bevacizumab: Case report and literature review," *Am J Kidney Disease*, 2007, 49:E23-E29.
Launay-Vacher and Deray, Hypertension and proteinuria: a class-effect of antiangiongenic therapies, *Anti-Cancer Drugs*, 2009, 20:81-82.
Martel et al., "Bevacizumab-related toxicities; association of hypertension and proteinuria," *Comm. Oncol.*, 2006, 3:90-93.
Sugimoto. "Neutralization of circulating vascular endothelial growth factor (VEGF) by Anti-VEGF antibodies and soluble VEGF receiptor 1 (sFit-1) induces proteinuria." *J. of Biol. Chem.* 2003, 278:12605-12608.
Zhu et al., "Risks of proteinuria and hypertension with bevacizumab, an antibody against vascular endothelial growth factor; systematic review and meta-analysis," *Am. J. of Kidney Diseases*, 2007, 49(2): 186-193.
International Search Report and Written Opinion in International Application No. PCT/US2010/061543, mailed Sep. 29, 2011, 8 pages.
International Preliminary Report on Patentability in International Application No. PCT/US2010/061543, issued Jun. 26, 2012, 5 pages.
Office Action in Australian Application No. 2010339723, issued Oct. 26, 2013, 3 pages.
Szeto et al., "Messenger RNA expression of glomerular podocyte markers in the urinary sediment of acquired proteinuric diseases," *Clin Chim Acta.*, 361(1-2):182-190, Nov. 2005.
International Preliminary Report on Patentability for PCT/US20131043727, dated Dec. 11, 2014, 5 pages.
Baelde et al., "Podocyte specific mRNA levels measured in urine of patients with preeclampsia are increased compared to healthy pregnant controls," *J Am Soc Nephrol.*, 21: 52A., Abstract F-FC225, 2010.
Barnidge et al., "Absolute quantification of the model biomarker prostate-specific antigen in serum by LC-Ms/MS using protein cleavage and isotope dilution mass spectrometry," *J Proteome Res.*, 3:644-652, May-Jun. 2004.
Barr et al., "Isotope dilution—mass spectrometric quantification of specific proteins: model application with apolipoprotein A-I," *Clin Chem.*, 42:1676-1682, Oct. 1996.
Bondar et al., "LC-MS/MS quantification of Zn-alpha2 glycoprotein: a potential serum biomarker for prostate cancer," *Clin Chem.*, 53: 673-678, Apr. 2007.
Boute et al., "NPHS2, encoding the glomerular protein podocin, is mutated in autosomal recessive steroid-resistant nephrotic syndrome," *Nat Genet.*, 24(4): 349-354, Apr. 2000.
Donoviel et al., "Proteinuria and perinatal lethality in mice lacking NEPH1, a novel protein with homology to NEPHRIN," *Mol Cell Biol.*, 21(14): 4829-4836, Jul. 2001.
Garovic et al., "Mass spectrometry as a novel method for detection of podocyturia in pre-eclampsia," *Nephrol Dial Transplant.*, 28(6):1555-1561, Epub Apr. 20, 2012.
Kerjaschki et al., "Identification and characterization of podocalyxin—the major sialoprotein of the renal glomerular epithelial cell," *J Cell Biol.*, 98(4):1591-1596, Apr. 1984.
Kuzyk et al., "Multiple reaction monitoring-based, multiplexed, absolute quantitation of 45 proteins in human plasma," *Mol Cell Proteomics.*, 8(8):1860-1877. Epub May 1, 2009.
Mundel and Shankland, "Podocyte biology and response to injury," *J Am Soc Nephrol.*, 13(12):3005-3015, Dec. 1, 2002.
Mundel et al., "Rearrangements of the cytoskeleton and cell contacts induce process formation during differentiation of conditionally immortalized mouse podocyte cell lines," *Exp Cell Res.*, 236(1): 248-258, Oct. 1997.
Mundel et al., "Synaptopodin: an actin-associated protein in telencephalic dendrites and renal podocytes," *J Cell Biol.*, 139(1): 193-204, Oct. 6, 1997.
Nakamura et al., "Urinary excretion of podocytes in patients with diabetic nephropathy," *Nephrol Dial Transplant.*, 15(9):1379-1383, Sep. 2000.
Seegmiller et al., "Quantification of urinary albumin by using protein cleavage and LC-MS/MS," *Clin Chem.*, 55(6):1100-1107, Epub Mar. 26, 2009.
Skoberne et al., "Glomerular epithelial cells in the urine: what has to be done to make them worthwhile?" *Am J Physiol Renal Physiol.*, 296(2):F230-F241, Epub Oct 8, 2008.
Zhao et al., "Altered nephrin and podoplanin distribution is associated with disturbed polarity protein PARD-3 and PARD-6 expressions in podocytes from preeclampsia," *Reprod Sci.*, 18(8):772-780, Epub Mar. 21, 2011.
Office Action in Japanese App. No. 2012-546149, mailed Jul. 23, 2014, 4 pages.

* cited by examiner

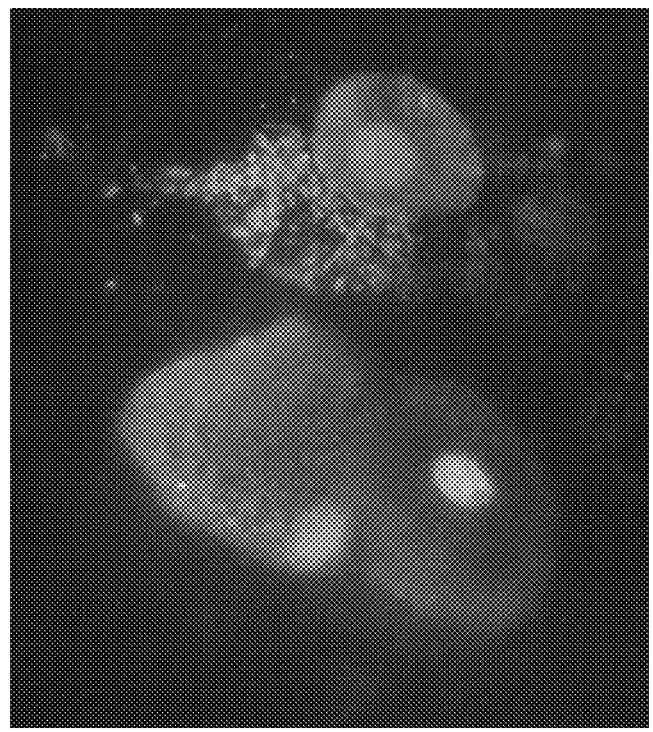

US 9,213,038 B2

EARLY MARKER OF PROTEINURIA IN PATIENTS TREATED WITH AN ANTI-VEGF TREATMENT

CROSS-REFERENCE TO RELATED APPLICATIONS

This application is a continuation of U.S. application Ser. No. 13/518,358, filed Jun. 21, 2012, which is a National Stage application under 35 U.S.C. 371 and claims benefit of International Application No. PCT/US2010/061543 having an International Filing Date of Dec. 21, 2010, which claims the benefit of U.S. Provisional Application Ser. No. 61/288,514, filed Dec. 21, 2009. The disclosures of the prior applications are considered part of (and are incorporated by reference in) the disclosure of this application.

BACKGROUND

1. Technical Field

This document relates to methods and materials involved in determining whether or not a human receiving an anti-VEGF therapy has podocyturia (e.g., urinary excretion of podocytes). For example, this document provides methods and materials for detecting the presence or absence of podocytes in a urine sample from a human receiving an anti-VEGF therapy to determine whether or not the human has developed or is at risk for developing proteinuria or kidney injury.

2. Background Information

Angiogenesis has a critical role in the growth, invasion, and metastasis of malignancies. Using angiogenesis inhibitors as an approach to cancer treatment has made significant progress in the field of cancer therapy. Agents that target the vascular endothelial growth factor (VEGF) signaling pathway are advancing in clinical development. However, a side effect in about 30% of cancer patients receiving anti-VEGF therapy is proteinuria (≥300 mg of total protein in a 24-hour urine sample). Proteinuria can be associated with characteristic renal pathologic changes of glomerular endotheliosis, leading to renal toxicity. One example of an anti-VEGF therapy is bevacizumab (Avastin®), a humanized recombinant monoclonal antibody directed against VEGF.

SUMMARY

This document provides methods and materials related to determining whether or not a human receiving an anti-VEGF therapy (e.g., bevacizumab) has developed or is at risk for developing proteinuria. For example, this document provides methods and materials for detecting urinary podocytes to determine whether or not a human receiving anti-VEGF therapy has or is at risk for developing proteinuria or kidney injury as indicated by podocyturia. Identifying patients who have podocyturia can allow such patients, who have or are at risk for developing toxicity as a result of the clinical use of drugs, to be treated effectively. In addition, identifying patients who do not have podocyturia can avoid unnecessary cessation of anti-VEGF therapy. As described herein, the presence of urinary podocytes can be used to identify humans receiving anti-VEGF therapy as having proteinuria or as being at risk for developing proteinuria as indicated by podocyturia.

In general, one aspect of this document features a method for assessing a human receiving an anti-VEGF therapy for a risk of developing proteinuria or renal injury. The method comprises, or consists essentially of, determining whether or not a urine sample from a human receiving anti-VEGF therapy contains urinary podocytes or evidence of urinary podocytes (e.g., podocyte remnants), wherein the presence of such podocytes indicates that the human is at risk for developing proteinuria.

In another aspect, this document features a method for assessing a human receiving an anti-VEGF therapy for proteinuria. The method comprises, or consists essentially of, determining whether or not a urine sample from a human receiving anti-VEGF therapy contains urinary podocytes or evidence of urinary podocytes (e.g., podocyte remnants), wherein the presence of such podocytes indicates that the human has proteinuria.

In another embodiment, this document describes a method for assessing a human receiving an anti-VEGF therapy for proteinuria, wherein the detection of proteinuria demonstrates renal injury.

The anti-VEGF therapy can be a bevacizumab therapy, a sunitinib therapy, a sorafenib therapy, or other known or effective therapies. The therapy may be a monoclonal or poloyclonal antibody therapy.

In another aspect, a human receiving an anti-epidermal growth factor receptor (EGFR) therapy, instead of or in addition to an anti-VEGF therapy, can be assessed for proteinuria or the risk of developing proteinuria or kidney injury as described herein with respect to an anti-VEGF therapy.

In some cases, podocytes can be detected in, for example, a urine sample using an antibody against a protein expressed by podocytes, such as podocin. In some cases, the antibody can be an antibody directed against a podocalyxin polypeptide, a nephrin polypeptide, or a synaptopodin polypeptide. Podocytes, or their fragments, can be detected using any appropriate method including, without limitation, cell staining techniques, immunocytochemistry techniques, and flow cytometry using, for example, anti-podocin antibodies.

In another aspect, this document features a method for assessing a human who has received an anti-VEGF therapy for a risk of developing proteinuria. The method comprises, or consists essentially of, determining whether or not a urine sample from a human receiving anti-VEGF therapy contains one or more urinary podocytes or evidence of one or more urinary podocytes, wherein the presence of the one or more urinary podocytes or the evidence indicates that the human is at risk for developing proteinuria. The anti-VEGF therapy can be selected from the group consisting of a bevacizumab therapy, a sunitinib therapy, and a sorafenib therapy. The determining step can comprise using an antibody to detect podocytes. The determining step can comprise using flow cytometry to detect podocytes. The antibody can be an anti-podocin antibody. The method can comprise detecting the presence of the one or more urinary podocytes. The method can comprise classifying the mammal as being at risk of developing proteinuria based at least in part on the presence of the one or more urinary podocytes. The method can comprise detecting the absence of the one or more urinary podocytes. The method can comprise classifying the mammal as not being at risk of developing proteinuria based at least in part on the absence of the one or more urinary podocytes. The human can be a non-pregnant human. The method can comprise determining whether or not the urine sample contains a level of urinary podocytes greater than about three or more urinary podocytes (e.g., greater than 3, 4, 5, 6, 7, 8, 9, 10, 11, 12, 13, 14, 15, or more urinary podocytes) per high power microscope field (400×).

In another aspect, this document features a method for assessing a human who has received an anti-VEGF or anti-EGFR therapy for proteinuria or a risk of developing proteinuria. The method comprises, or consists essentially of, determining whether or not a urine sample from a human receiving anti-VEGF therapy or an anti-EGFR therapy contains one or more urinary podocytes or evidence of one or more urinary podocytes, classifying the human as having or as being at risk of developing proteinuria if the one or more urinary podocytes or the evidence are present in the urine sample, and classifying the human as not having or as not being at risk of developing proteinuria if the one or more urinary podocytes and the evidence are not present in the urine sample. The human can be a human who received the anti-VEGF therapy. The anti-VEGF therapy can be selected from the group consisting of a bevacizumab therapy, a sunitinib therapy, and a sorafenib therapy. The determining step can comprise using an antibody to detect podocytes. The antibody can be an anti-podocin antibody. The determining step can comprise using flow cytometry to detect podocytes. The method can comprise detecting the presence of the one or more urinary podocytes. The method can comprise detecting the absence of the one or more urinary podocytes. The human can be a non-pregnant human. The method can comprise determining whether or not the urine sample contains a level of urinary podocytes greater than about three or more urinary podocytes (e.g., greater than 3, 4, 5, 6, 7, 8, 9, 10, 11, 12, 13, 14, 15, or more urinary podocytes) per high power microscope field (400×).

In another aspect, this document features a method for identifying a human who has received an anti-VEGF or anti-EGFR therapy as having proteinuria or a risk of developing proteinuria. The method comprises, or consists essentially of, detecting the presence of one or more podocytes in a urine sample of a human who received anti-VEGF therapy or an anti-EGFR therapy, and classifying the human as having or as being at risk of developing proteinuria based at least in part on the presence. The human can be a human who received the anti-VEGF therapy. The anti-VEGF therapy can be selected from the group consisting of a bevacizumab therapy, a sunitinib therapy, and a sorafenib therapy. The detecting step can comprise using an antibody to detect the one or more podocytes. The antibody can be an anti-podocin antibody. The detecting step can comprise using flow cytometry to detect the one or more podocytes. The human can be a non-pregnant human. The presence of the one or more podocytes in the urine sample can be detected by detecting the presence of remnants of one or more urinary podocytes. The method can comprise determining whether or not the urine sample contains a level of urinary podocytes greater than about three or more urinary podocytes (e.g., greater than 3, 4, 5, 6, 7, 8, 9, 10, 11, 12, 13, 14, 15, or more urinary podocytes) per high power microscope field (400×).

Unless otherwise defined, all technical and scientific terms used herein have the same meaning as commonly understood by one of ordinary skill in the art to which this invention pertains. Although methods and materials similar or equivalent to those described herein can be used to practice the invention, suitable methods and materials are described below. All publications, patent applications, patents, and other references mentioned herein are incorporated by reference in their entirety. In case of conflict, the present specification, including definitions, will control. In addition, the materials, methods, and examples are illustrative only and not intended to be limiting.

The details of one or more embodiments of the invention are set forth in the accompanying drawings and the description below. Other features, objects, and advantages of the invention will be apparent from the description and drawings, and from the claims.

DESCRIPTION OF THE DRAWINGS

FIG. 1 contains a photograph of urinary cells plated on a collagen-coated slide, cultured for 24 hours, and stained for podocin immunoreactivity.

DETAILED DESCRIPTION

This document provides methods and materials for determining whether or not a human who received or is receiving an anti-VEGF therapy has developed or is at risk for developing proteinuria as indicated by podocyturia. For example, this document provides methods and materials for determining whether or not a human (e.g., a non-pregnant cancer patient) treated with an anti-VEGF therapy has an elevated level of urinary podocytes, thereby indicating that the human has developed or is at risk for developing proteinuria. As disclosed herein, the detection of one or more podocytes or evidence of podocytes (e.g., podocyte remnants) in the urine of a human is indicative that the human developed or is at risk of developing proteinuria. The presence of proteinuria may indicate that the human is experiencing or at risk of developing renal injury. Severe proteinuria may be indicative of nephrotic syndrome.

The methods and materials provided herein can be used to assess any type of human who received or is receiving an anti-VEGF therapy, an anti-EGFR therapy, or a combination of an anti-VEGF therapy and an anti-EGFR therapy. For example, the methods and materials provided herein can be used to assess male or female humans for proteinuria or a risk of developing proteinuria. In some cases, the methods and materials provided herein can be used to assess non-pregnant humans who received or are receiving an anti-VEGF therapy, an anti-EGFR therapy, or a combination of an anti-VEGF therapy and an anti-EGFR therapy for proteinuria or a risk of developing proteinuria. Examples of anti-VEGF therapies include, without limitation, bevacizumab therapies, sunitinib therapies, and sorafenib therapies. Examples of anti-EGFR therapies include, without limitation, cetuximab therapies, panitumumab therapies, trastuzumab therapies, lapatinib therapies, erlotinib therapies, and geftinib therapies.

Any appropriate method can be used to determine the level of podocytes in a human's urine. For example, cell staining techniques that include using antibodies that bind to podocytes or polypeptides expressed by podocytes can be used. Examples of such antibodies include, without limitation, antibodies that have the ability to bind a podocin polypeptide (e.g., GenBank GI No. 7657615; Accession No. NP_055440.1), a podocalyxin polypeptide (e.g., GenBank GI No. 66277202, Accession No. NP_001018121.1; GenBank GI No. 33598950, Accession No. NP_005388.2; GenBank GI No. 7271815, Accession No. AAB61574.1; and GenBank GI No. 7657465, Accession No. NP_056535.1), a nephrin polypeptide (e.g., GenBank GI No. 10441644; Accession No. AAG17141.1), a synaptopodin polypeptide (e.g., GenBank GI No. 33323347; Accession No. AAQ07403.1), a Neph1 polypeptide (e.g., GenBank GI No. 14572521; Accession No. AAK00529.1), a GLEPP1 polypeptide (e.g., GenBank GI No. 885926; Accession No. AAA82892.1), a WT1 polypeptide (e.g., GenBank GI No. AAH46461.2; Accession No. 110611793), a CD2AP polypeptide (e.g., GenBank GI No. 11321634; Accession No. NP_036252.1), an actin polypeptide (e.g., GenBank GI No. 4501881; Accession No. NP_001091.1), an actinin polypeptide (e.g., GenBank GI No. 3157976; Accession No. AAC17470.1), a cadherin polypeptide (e.g., GenBank GI No. 2281027; Accession No. BAA21569.1), a catenin polypeptide (e.g., GenBank GI No. 4503131; Accession No. NP_001895.1), an integrin polypeptide (e.g., GenBank GI No. 47078292; Accession No. NP_000203.2), a vinculin polypeptide (e.g., GenBank GI No. 340237; Accession No. AAA61283.1), a talin polypeptide (e.g., GenBank GI No. 6682361; Accession No. AAF23322.1), a paxillin polypeptide (e.g., GenBank GI No. 704348; Accession No. AAC50104.1), or a ZO-1 polypeptide (e.g., GenBank GI No. 116875767; Accession No. NP_003248.3). In some cases, flow cytometry techniques can be used to determine the level of podocytes present in a human urine sample. The podocytes detected in a urine sample can be viable podocytes, non-viable podocytes, or a combination thereof. In some cases, non-viable podocytes can be identifiable podocyte remnants.

An antibody can be, without limitation, a polyclonal, monoclonal, human, humanized, chimeric, or single-chain antibody, or an antibody fragment having binding activity, such as a Fab fragment, F(ab') fragment, Fd fragment, fragment produced by a Fab expression library, fragment comprising a VL or VH domain, or epitope binding fragment of any of the above. An antibody can be of any type (e.g., IgG, IgM, IgD, IgA or IgY), class (e.g., IgG1, IgG4, or IgA2), or subclass. In addition, an antibody can be from any animal including, without limitation, birds and mammals. For example, an antibody can be a human, rabbit, sheep, or goat antibody. An antibody can be naturally occurring, recombinant, or synthetic. Antibodies can be generated and purified using any appropriate method. For example, monoclonal antibodies can be prepared using hybridoma, recombinant, or phage display technologies, or a combination of such technologies. In some cases, antibody fragments can be produced synthetically or recombinantly from a gene encoding a partial antibody sequence. Any antibody that can be used to detect podocytes (e.g., anti-podocin antibodies, anti-podocalyxin antibodies, anti-nephrin antibodies, or anti-synaptopodin antibodies) can have a binding affinity for its antigen of at least $10^4$ mol$^{-1}$(e.g., at least $10^1$, $10^6$, $10^7$, $10^8$, $10^9$, $10^{10}$, $10^{11}$, or $10^{12}$ mol$^{-1}$). For example, an anti-podocin antibody that binds to podocin polypeptides at an affinity of at least $10^4$ mol$^{-1}$(e.g., at least $10^1$, $10^6$, $10^7$, $10^8$, $10^9$, $10^{10}$, $10^{11}$, or $10^{12}$ mol$^{-1}$) can be used as described herein.

The term "elevated level" as used herein with respect to the level of urinary podocytes is any level that is above a median level of podocytes present in urine from a random population of non-pregnant humans known not to have proteinuria (e.g., a random population of 5, 10, 15, 20, 30, 40, 50, 100, 500, or more non-pregnant humans known not to have proteinuria). For example, the random population of non-pregnant humans can be a population of non-pregnant humans receiving an anti-VEGF therapy or a population of non-pregnant humans not receiving an anti-VEGF therapy, provided that the humans do not have proteinuria. In some cases, the random population of non-pregnant humans can be a population of non-pregnant humans receiving an anti-EGFR therapy or a population of non-pregnant humans not receiving an anti-EGFR therapy, provided that the humans do not have proteinuria. In some cases, an elevated level of urinary podocytes can be a detectable level of podocytes (e.g., podocin-positive cells) within a urine sample. The presence or absence of such a detectable level of podocytes (e.g., podocin-positive cells) can be determined using an anti-podocin antibody.

Once the level of urinary podocytes of a human is determined, then the level can assessed to determine if the level is an elevated level. The presence of an elevated level of urinary podocytes can indicate that the human has proteinuria or a risk of developing proteinuria. Additional clinical tests can be performed to confirm that a human having an elevated level of urinary podocytes has proteinuria. For example, a total protein determination in a 24-hour urine collection test, a urine dipstick protein analysis test, and/or a protein-creatinine ratio test in a random urine sample can be performed to confirm that a human having an elevated level of urinary podocytes has proteinuria. If the presence of proteinuria is confirmed by an additional clinical test (e.g., a total protein determination in a 24-hour urine collection test) for a human having an elevated level of urinary podocytes, then that human can be classified as having proteinuria. If the presence of proteinuria is not confirmed by an additional clinical test (e.g., a total protein determination in a 24-hour urine collection test) for a human having an elevated level of urinary podocytes, then that human can be classified as being at risk of developing proteinuria.

In some cases, the level of urinary podocytes present within a human can be assessed using a cutoff value such as 0.85 urinary podocytes present per mg creatinine. For example, once the level of urinary podocytes of a human is determined, the level can compared to a cutoff value (e.g., 0.85 urinary podocytes/mg creatinine) The presence of a level of urinary podocytes greater than or equal to the cutoff value can indicate that the human has proteinuria or a risk of developing proteinuria. Additional clinical tests can be performed to confirm that a human having a level of urinary podocytes greater than or equal to the cutoff value has proteinuria. For example, a total protein determination in a 24-hour urine collection test, a urine dipstick protein analysis test, and/or a protein-creatinine ratio test in a random urine sample can be performed to confirm that a human having a level of urinary podocytes greater than or equal to the cutoff value has proteinuria. If the presence of proteinuria is confirmed by an additional clinical test (e.g., a total protein determination in a 24-hour urine collection test) for a human having a level of urinary podocytes greater than or equal to the cutoff value, then that human can be classified as having proteinuria. If the presence of proteinuria is not confirmed by an additional clinical test (e.g., a total protein determination in a 24-hour urine collection test) for a human having a level of urinary podocytes greater than or equal to the cutoff value, then that human can be classified as being at risk of developing proteinuria.

In some cases, a human treated with an anti-VEGF therapy, an anti-EGFR therapy, or both can be classified as having proteinuria or a risk of developing proteinuria if it is determined that the podocyte level in a urine sample from the human treated with the therapy (e.g., the anti-VEGF therapy, anti-EGFR therapy, or both) is greater than the podocyte level in a urine sample obtained from that human at an earlier time point (e.g., at a time prior to any treatments with an anti-VEGF therapy or an anti-EGFR therapy). Additional clinical tests can be performed to confirm that a human experiencing such an increase in urinary podocytes over time has proteinuria. For example, a total protein determination in a 24-hour urine collection test, a urine dipstick protein analysis test, and/or a protein-creatinine ratio test in a random urine sample can be performed to confirm that a human experiencing an increase in urinary podocytes over time has proteinuria. If the presence of proteinuria is confirmed by an additional clinical test (e.g., a total protein determination in a 24-hour urine collection test) for a human experiencing an increase in urinary podocytes over time, then that human can be classified as having proteinuria. If the presence of proteinuria is not confirmed by an additional clinical test (e.g., a total protein determination in a 24-hour urine collection test) for a human experiencing an increase in urinary podocytes over time, then that human can be classified as being at risk of developing proteinuria.

In some cases, the detection of one or more podocytes in a urine sample can be indicative of podocyturia. For example, a non-pregnant patient receiving an anti-VEGF therapy or anti-EGFR therapy (or both) can be classified as having proteinuria or a risk of developing proteinuria based at least in part on the detection of one or more podocytes in a urine sample. Additional clinical tests can be performed to confirm that a human having one or more detectable urinary podocytes has proteinuria. For example, a total protein determination in a 24-hour urine collection test, a urine dipstick protein analysis test, and/or a protein-creatinine ratio test in a random urine sample can be performed to confirm that a human having one or more detectable urinary podocytes has proteinuria. If the presence of proteinuria is confirmed by an additional clinical test (e.g., a total protein determination in a 24-hour urine collection test) for a human having one or more detectable urinary podocytes, then that human can be classified as having proteinuria. If the presence of proteinuria is not confirmed by an additional clinical test (e.g., a total protein determination in a 24-hour urine collection test) for a human having one or more detectable urinary podocytes, then that human can be classified as being at risk of developing proteinuria.

A human treated with an anti-VEGF therapy, an anti-EGFR therapy, or both can be monitored using the methods and materials provided herein. Podocytes may appear in a patient's urine before any proteinuria is detected, thus providing an early predictor of a pending adverse event. This early indication may allow health care personnel to alter a patient's anti-VEGF or anti-EGFR treatment plan or to begin treatment for proteinuria. For example, the level of podocytes in a urine sample can be assessed to determine whether or not proteinuria persists in response to decreasing the dose of anti-VEGF therapy or anti-EGFR therapy.

This document also provides methods and materials to assist medical or research professionals in determining whether or not a human treated with an anti-VEGF therapy, an anti-EGFR therapy, or both has or is developing proteinuria. Medical professionals can be, for example, doctors, nurses, medical laboratory technologists, and pharmacists. Research professionals can be, for example, principal investigators, research technicians, postdoctoral trainees, and graduate students. A professional can be assisted by (1) determining the level of urinary podocytes in a urine sample, and (2) communicating information about the level to that professional. In some cases, a professional can be assisted by (1) assessing a urine sample of the presence of urinary podocytes, and (2) communicating information about the presence of urinary podocytes to that professional.

Any appropriate method can be used to communicate information to another person (e.g., a professional). For example, information can be given directly or indirectly to a professional. In addition, any type of communication can be used to communicate the information. For example, mail, e-mail, telephone, and face-to-face interactions can be used. The information also can be communicated to a professional by making that information electronically available to the professional. For example, the information can be communicated to a professional by placing the information on a computer database such that the professional can access the information. In addition, the information can be communicated to a hospital, clinic, or research facility serving as an agent for the professional.

This document also provides methods and materials for treating humans with an anti-VEGF therapy such as bevacizumab, an anti-EFGR therapy, or both under conditions that reduce the likelihood of inducing proteinuria. For example, a human needing an anti-VEGF therapy (e.g., a human cancer patient needing bevacizumab treatment) can be administered a standard dose of bevacizumab (e.g., 5-15 mg/kg/day) for a limited number of dosing cycles administered once every week, every two weeks, or every three weeks. At least once within the first 3 days of treatment, a urine sample can be obtained and assessed for urinary podocytes as described herein. If urinary podocytes are detected or an elevated level of urinary podocytes is detected, then the dose of the anti-VEGF therapy can be reduced by at least 30 percent (e.g., 30, 40, 50, 75, 80, 90, or 100 percent) for a period of time. Alternatively, anti-VEGF therapy can be skipped for one or two dosing cycles for a period of time so medication is received every four weeks or every six weeks. After this period of time, a urine sample can be obtained and assessed for urinary podocytes as described herein. If urinary podocytes are not detected or an elevated level of urinary podocytes is not detected, then the dose of the anti-VEGF therapy can be increased (e.g., increased to the original dose or to some degree less than the original dose). If urinary podocytes are detected or an elevated level of urinary podocytes is detected, then the dose or the frequency of the anti-VEGF therapy can be reduced further for an additional period of time (e.g., once every week, every two weeks, every three weeks, or more cycles). The assessment of urine for urinary podocytes or urinary podocyte levels and the adjustment of anti-VEGF therapy dosage can be repeated multiple times until a dose of anti-VEGF therapy is reached that does not induce proteinuria as determined by the presence or level of urinary podocytes detected.

It is noted that while the methods and materials described are understood for patients receiving anti-VEGF therapy, anti-EGFR therapy, or both, patients receiving other therapies, such as non-steroidal anti-inflamatory drugs, bisphosphonate, trastuzumab, capecitabine, paclitaxel, or anthracycline therapy may also be assessed for having proteinuria or being at risk for developing proteinuria as indicated by podocyturia.

The invention will be further described in the following examples, which do not limit the scope of the invention described in the claims.

EXAMPLES

Example 1

A Case of Podocyturia in a Patient Receiving Anti-VEGF Therapy with Sunitinib

Case Study

A 67 year old female presented with a 7.2×6.1 cm mass involving the central and lower portion of the right kidney. Renal function was normal with a creatinine of 1.0 and no proteinuria. She subsequently underwent a right radical nephrectomy and retroperitoneal lymphadenectomy. Pathology confirmed Grade 2, T2, N0, M1 renal cell carcinoma, clear cell type. Sunitinib therapy was initiated, with good response.

Four months into therapy, renal function worsened with a peak creatinine of 1.5 and 467 mg of protein in 24 hours. Angiotensin receptor blockade with Diovan was initiated. Additional side effects included hypertension, hand and foot syndrome, and drug-induced hypothyroidism.

After seven months of therapy, her creatinine improved to 1.3 but she remained proteinuric, with a predicted 24 hour protein of 931 mg. At that time, a podocyturia assay was performed as described below and the presence of urinary podocytes was confirmed (FIG. 1).

Detection of Podocytes

A random urine sample (25-50 mL each) was centrifuged for 8 minutes at 700 g at room temperature. The pellets were rinsed twice with human diploid fibroblast (HDF) solution. Next, the pellets were resuspended in Dulbecco's modified eagle's medium (DMEM) F-12 medium with 10% fetal bovine serum that was supplemented with antibiotics for the prevention of bacterial contamination. A one-milliliter aliquot was plated on a collagen-coated tissue culture slide, which was followed by overnight incubation at 37° C. in 5% $CO_2$. The next day, the media were removed, followed by two phosphate-buffered saline solution washes. The slide was fixed with 1 mL of ice cold methanol for 10 minutes at −20° C. The slide was incubated with antibodies to podocin (dilution, 1:200). After being washed with phosphate-buffered saline solution, a secondary fluorescein isothiocyanate-labeled antibody was added at a dilution of 1:40 for 30 minutes.

The sediment was counterstained with Hoechst nuclear stain to facilitate differentiation of whole cells from cell fragments. Coverslips were mounted with Vectashield (Vector Labs, Burlington, Calif.), and the slides were viewed with a fluorescence microscope (Leica, Germany). Nucleated, positive-staining cells were considered to be podocytes. A renal pathologist, who was blinded to the clinical diagnosis and laboratory findings, evaluated each sample to determine the number of cells that were present and the percentage of cells that were stained for podocin.

For the patient presented, the regimen of Sunitinib was changed, and the dose was decreased. Her kidney function, as per creatinine measurements, improved. She remains proteinuric, but her kidney function remains stable.

A test is positive for proteinuria if the number of podocytes expressed as a ratio to the creatinine content of the respective urine sample is greater than 0.85 podocytes/mg creatinine.

The results provided herein indicated that an elevated level of urinary podocytes is a marker of proteinuria in humans being treated with an anti-VEGF therapy. In controls, two patients on anti-VEGF therapy without proteinuria, podocyturia was not observed.

Example 2

Podocyturia in Patients Treated with VEGF Blocking Therapy for Cancer

The following was performed to determine whether podocyturia is present in patients who, while undergoing anti-VEGF therapy, develop proteinuria (Table 1). In addition, urinary podocyte excretion was compared among patients on anti-VEGF therapy with proteinuria ranging from 101 to 9720 mg/d (Table 1).

TABLE 1

| Type of Cancer | Age/Sex | Anti-VEGF | GFR | Proteinuria | Cells/HPF |
| --- | --- | --- | --- | --- | --- |
| Cholangio | 68/F | B | 66 | 420 mg/d | 0 |
| Renal Cell | 60/M | S/nib | 39 | 101 mg/d | 1 |
| Colorectal | 55/F | B | 137 | 1 + dipstick | 1 |
| Colon | 66/F | B + S/nib | 77 | 330 mg/d | 0 |
| GBM | 59/F | B + S/nib | 78 | 152 mg/d | 1 |
| Renal Cell | 73/M | B | 63 | 2144 mg/d | >3 |
| Renal Cell | 67/F | Sunitib | 43 | 2112 mg/d | >3 |
| SBC | 68/M | B | 59 | 6361 mg/d | >3 |
| GBM | 70/M | S/nib | 70 | 9720 mg/d | >9 |

GBM: glioblastoma multiforme;
SBC: small bowel carcinoid;
B: bevacizumab;
S/nib: sorafenib;
HPF: 400x high power field.

These results demonstrate a higher degree of podocyturia in patients undergoing anti-VEGF therapy with proteinuria in excess of 2 gr/d compared to those treated with the same agents and proteinuria <0.5 gr/d.

OTHER EMBODIMENTS

It is to be understood that while the invention has been described in conjunction with the detailed description thereof, the foregoing description is intended to illustrate and not limit the scope of the invention, which is defined by the scope of the appended claims. Other aspects, advantages, and modifications are within the scope of the following claims.

What is claimed is:

1. A method for using an anti-VEGF therapy, without inducing proteinuria, to treat cancer in a human having cancer, wherein said method comprises:
   (a) administering an initial dose of said anti-VEGF therapy to said human to treat said cancer,
   (b) obtaining a urine sample from said human receiving said anti-VEGF therapy,
   (c) contacting said urine sample with an antibody that binds to podocytes or polypeptides expressed by podocytes to form an antigen-antibody complex, if podoycytes or polypeptides expressed by podocytes are present in said sample,
   (d) detecting, by flow cytometry, the presence of said antigen-antibody complex, thereby identifying said human as being at risk of developing proteinuria, if said complex is detected and
   (e) administering a subsequent dose of said anti-VEGF therapy to said human who does not have proteinuria, but in whom the antigen-antibody complex has been detected, wherein said subsequent dose is at least 30 percent lower than said initial dose.

2. The method of claim 1, wherein said method is a method for treating a human with said anti-VEGF therapy, wherein said method comprises administering an initial dose of said anti-VEGF therapy, and wherein said method comprises administering a subsequent dose of said anti-VEGF therapy.

3. The method of claim 2, wherein said anti-VEGF therapy is selected from the group consisting of a bevacizumab therapy, a sunitinib therapy, and a sorafenib therapy.

4. The method of claim 1, wherein said human is a non-pregnant human.

5. The method of claim 1, wherein said administering said initial dose comprises administering between 5 and 15 mg of said anti-VEGF therapy per kg of body weight of said human per day once every week, once every two weeks, or once every three weeks.

6. The method of claim 1, wherein said urine sample is obtained from said human within at least three days of administration of said initial dose.

7. The method of claim 1, wherein said antibody is an anti-podocin antibody.

* * * * *

UNITED STATES PATENT AND TRADEMARK OFFICE
CERTIFICATE OF CORRECTION

| | | |
|---|---|---|
| PATENT NO. | : 9,213,038 B2 | Page 1 of 1 |
| APPLICATION NO. | : 13/898124 | |
| DATED | : December 15, 2015 | |
| INVENTOR(S) | : Vesna D. Garovic | |

It is certified that error appears in the above-identified patent and that said Letters Patent is hereby corrected as shown below:

In the specification

Column 1, line 10, after U.S.C. insert -- § --.

In the claims

Column 10, line 22 (Claim 1), please delete "podoycytes" and insert -- podocytes --, therefor.

Signed and Sealed this
Second Day of August, 2016

Michelle K. Lee
*Director of the United States Patent and Trademark Office*